US011542519B2

(12) United States Patent
Denolf et al.

(10) Patent No.: US 11,542,519 B2
(45) Date of Patent: Jan. 3, 2023

(54) ANTHER-SPECIFIC PROMOTER AND USES THEREOF

(71) Applicant: BASF SE, Ludwigshafen (DE)

(72) Inventors: Peter Denolf, Ghent (BE); Sandy Vanderauwera, Ghent (BE); Claus Frohberg, Ghent (BE); Marie-Therese Scheirlinck, Ghent (BE); Sigrid Vanhoutte, Ghent (BE)

(73) Assignee: BASF SE, Ludwigshafen (DE)

(*) Notice: Subject to any disclaimer, the term of this patent is extended or adjusted under 35 U.S.C. 154(b) by 290 days.

(21) Appl. No.: 16/496,101

(22) PCT Filed: Mar. 15, 2018

(86) PCT No.: PCT/EP2018/056537
§ 371 (c)(1),
(2) Date: Sep. 20, 2019

(87) PCT Pub. No.: WO2018/172181
PCT Pub. Date: Sep. 27, 2018

(65) Prior Publication Data
US 2020/0095596 A1 Mar. 26, 2020

(30) Foreign Application Priority Data
Mar. 23, 2017 (EP) .................................. 17162487

(51) Int. Cl.
*C12N 15/82* (2006.01)

(52) U.S. Cl.
CPC .............................. *C12N 15/8231* (2013.01)

(58) Field of Classification Search
None
See application file for complete search history.

(56) References Cited

U.S. PATENT DOCUMENTS

| | | | |
|---|---|---|---|
| 4,757,011 A | 7/1988 | Chaleff et al. | |
| 4,769,061 A | 9/1988 | Comai | |
| 4,940,835 A | 7/1990 | Shah et al. | |
| 4,971,908 A | 11/1990 | Kishore et al. | |
| 5,593,874 A | 1/1997 | Brown et al. | |
| 5,641,876 A | 6/1997 | McElroy et al. | |
| 5,652,354 A | 7/1997 | Mariani et al. | |
| 5,659,122 A | 8/1997 | Austin | |
| 5,760,190 A * | 6/1998 | Neill | C07K 14/415 530/370 |
| 6,423,885 B1 | 7/2002 | Waterhouse et al. | |
| 2004/0203141 A1* | 10/2004 | Dubcovsky | C12N 15/8237 435/320.1 |
| 2005/0144667 A1 | 6/2005 | Stanley et al. | |
| 2014/0173781 A1* | 6/2014 | Cho | C12N 15/8216 800/300 |

FOREIGN PATENT DOCUMENTS

| | | |
|---|---|---|
| EP | 0242236 A1 | 10/1987 |
| EP | 0242246 A1 | 10/1987 |
| EP | 0507698 A1 | 10/1992 |
| EP | 0508909 A1 | 10/1992 |
| WO | WO-99/53050 A1 | 10/1999 |
| WO | WO-01/12824 A1 | 2/2001 |
| WO | WO-03/076619 A1 | 9/2003 |
| WO | WO-2004/073390 A1 | 9/2004 |
| WO | WO-2005/047505 A2 | 5/2005 |
| WO | WO-2005/049842 A2 | 6/2005 |
| WO | WO-2005/052170 A2 | 6/2005 |
| WO | WO-2006/074400 A2 | 7/2006 |
| WO | WO-2016/193798 | 12/2016 |

OTHER PUBLICATIONS

Szucs et al. Validation of the VRN-H2/RN-H1 epistatic model in barley reveals that intron length variation in VRN-H1 may account for a continuum of vernalization sensitivity. Molecular Genetics Genomics. 2007. 277:249-261.*
Alonso-Peral et al. The promoter of the cereal VERNALIZATION1 gene is sufficient for transcriptional induction by prolonged cold. PLoS One. 2011. 6(12):e29456 (pp. 1-9).*
Kempe et al 2013 (Transgenic Research 22: pp. 1089-1105) (Year: 2013).*
Hu et al 1997 (PlantCell Reports 16: pp. 520-525) (Year: 1997).*
Alonso-Peral et al., The promoter of the cereal VERNALIZATION1 gene is sufficient for transcriptional induction by prolonged cold, PLoS One, 6(12):e29456 (2011).
Barta et al., "DoOP: Databases of Orthologous Promoters, collections of clusters of orthologous upstream sequences from chordates and plants", Nucleic Acids Research, vol. 33, Issue suppl_1, Jan. 2005, pp. D86-D60.
Hsu et al., "Identification of the tapetum/microspore-specific promoter of the pathogenesis-related 10 gene and its regulation in the anther of Lilium longiflorum", Plant Science, vol. 215-216, Feb. 2014, pp. 124-133.
International Application No. PCT/EP2018/056537, International Search Report and Written Opinion, dated May 14, 2018.
Ishida et al., "Wheat (Triticum aestivum L.) Transformation Using Immature Embryos", Agrobacterium Protocols, vol. 1223, 2014, pp. 189-198.
Liu et al., "The rice OsLTP6 gene promoter directs anther-specific expression by a combination of positive and negative regulatory elements", Planta, vol. 238, Issue 5, Nov. 2013, pp. 845-857.
Maheshwari et al., "In Vitro Culture of Wheat and Genetic Transformation—Retrospect and Prospect", Critical Reviews in Plant Sciences, vol. 14, Issue 2, 1995, pp. 149-178.

(Continued)

*Primary Examiner* — Matthew R Keogh
(74) *Attorney, Agent, or Firm* — Marshall, Gerstein & Borun LLP

(57) ABSTRACT

The present invention relates to barley sequences comprising anther-specific promoter activity. Provided are recombinant genes comprising the anther-specific promoter operably linked to a heterologous nucleic acid sequence, and cells, plants and seeds comprising the recombinant gene. The promoters can be used to alter gene expression specifically in the anthers.

13 Claims, 1 Drawing Sheet
Specification includes a Sequence Listing.

(56) References Cited

OTHER PUBLICATIONS

Manimaran et al., "Identification of cis-elements and evaluation of upstream regulatory region of a rice anther-specific gene, OSIPP3, conferring pollen-specific expression in *Oryza sativa*(L.) ssp. indica", Plant Reproduction, vol. 28, Issue 3-4, Dec. 2015, pp. 133-142.

Needleman et al., "A general method applicable to the search for similarities in the amino acid sequence of two proteins", Journal of Molecular Biology, vol. 48, Issue 3, Mar. 28, 1970, pp. 443-453.

Nehra et al., "Selffertile transgenic wheat plants regenerated from isolated scutellar tissues following microprojectile bombardment with two distinct gene constructs", The Plant Journal, vol. 5, Issue 2, Feb. 1994, pp. 285-297.

Pearson et al., "Improved tools for biological sequence comparison", Proceedings of the National Academy of Sciences of the United States of America, vol. 85, Issue 8, Apr. 1988, pp. 2444-2448.

Yau et al., "Less is more: strategies to remove marker genes from transgenic plants", BMC Biotechnology, vol. 13, Issue 36, Dec. 2013, p. 23.

Yue et al., "Characterization of a novel anther-specific gene encoding a leucine-rich repeat protein in petunia", Genetics and Molecular Research, vol. 13, Issue 4, 2014, pp. 9889-9898.

Zaidi et al., "Investigating Triticeae anther gene promoter activity in transgenic Brachypodium distachyon", Planta, vol. 245, Issue 2, Feb. 2017, pp. 385-396.

\* cited by examiner

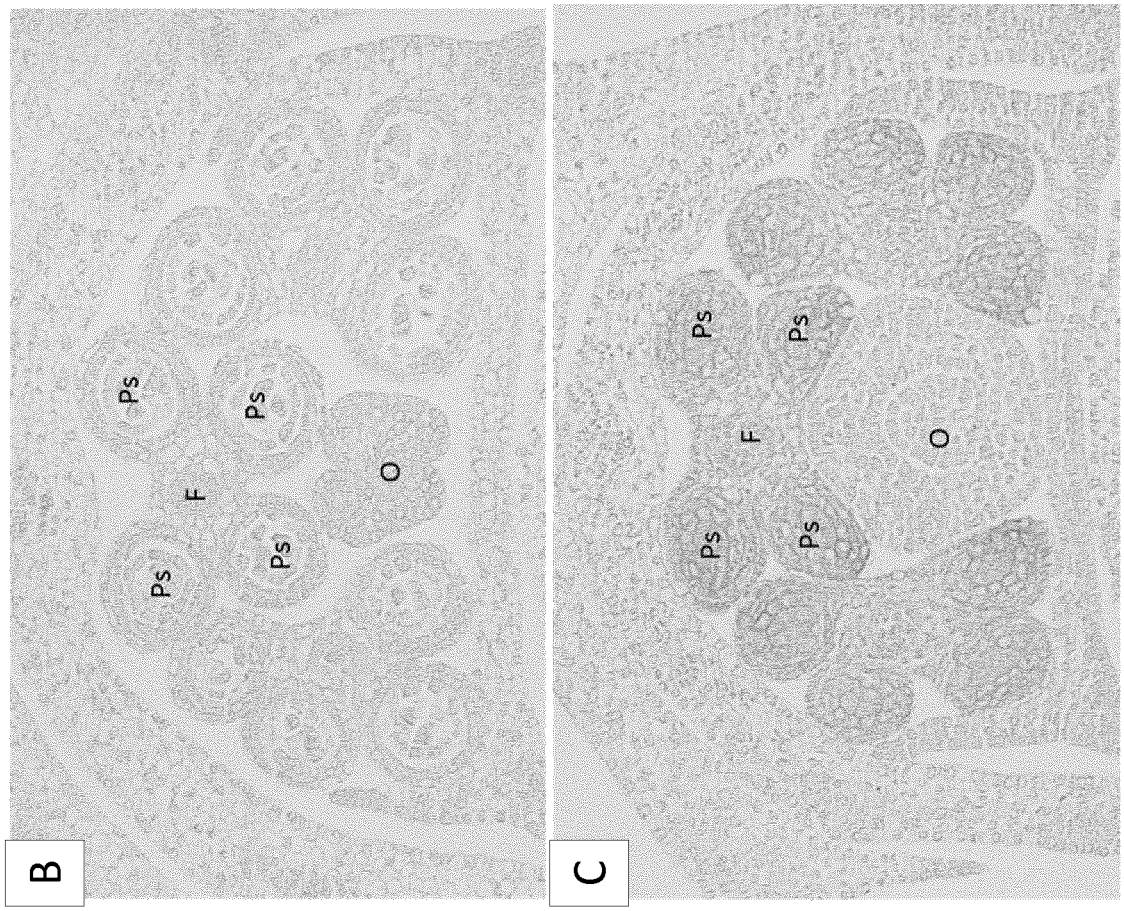
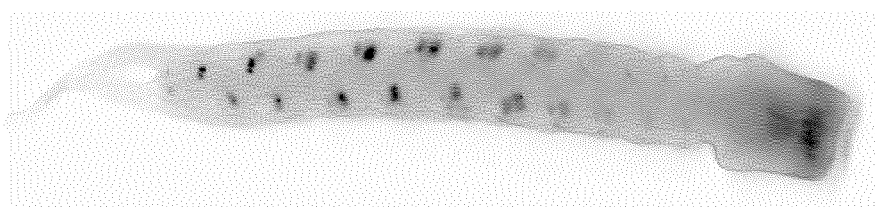

SEQUENCE LISTING

<160> NUMBER OF SEQ ID NOS: 2

<210> SEQ ID NO 1
<211> LENGTH: 1998
<212> TYPE: DNA
<213> ORGANISM: Hordeum vulgare

<400> SEQUENCE: 1

```
ctagttccca atttaagagt ggattatttg atcacgggat catctattcc ctataaaact      60
ttgagatgtt ttctatgaag tatggtttac acagtatatc tgatctaaat attggttttg     120
cattcttgga aacacactgc aaagtttagg gatgctcatg tttgtatctt ttcaatcata     180
gagatatact ccctccgtcc gtcaaaaact gtgcatctaa cagtatattt tttttccata     240
aagagtgtac atctacattt tctatgcgct tagcttttaa tttaaccggt attaagtgac     300
taatgtagta acttgtgctc tagctattgg ctgcatgcct aaccttaatt actgcatgca     360
gcaacgttca tttaatcttc ttttctcaat ggttgtatgt acacataagt ctgttatttt     420
tgtacaataa ttatgtcatg gaggtctttc ttggtctatg tgcaaatctc tgtatgcacg     480 gttttttggcg gacggaggga gtacacgaca tattcacaag caaaaaagaa aaagttggac     540
atggcatatt cgcaaaaaaa gaaataagaa aagagaagag atgtgcatgg catgattgtg     600
aaacctatcc tcatcgatcg taaaaagcgg tattggtatt tttaggggaa taaagagcgc     660
tattggtggt tgctggttac atcgaatggt tgcaaagtgg tcatttgaca agcacgcatg     720
tgggctttat ctgtttgtca tcataaacga taaatgggtc aagattcaca gatcagagaa     780
tacgtcgtca aagtctcgaa cacttcactg cgtggtctac tgggcccaat agcagtttta     840
gtgaacaaac cattttagtg ctgcaatagt ttcagcacga tccttccctt tgtaccgaga     900
agccggtcac cgcagatata tcacatgcac tttccgcatt tttttaatat tatatcacat     960
gcacagttct acaagacata cacagagcgt ttatttttt tgtgagaagg aaaacacatg    1020
agccgtttca acatcgcatg attcgacgct gggcaacagt gtattgatgg gtggaggact    1080
ggtcggcgca cacgcgcgca cagtacccct actccggcgg gagtatcttc cattcattcc    1140
agaaatacgc gggtcggcca aaagtagaaa aatacactgc gccgacccaa cccacacgca    1200
gcaacggttc gcgtcaaaag tccagctcgc gtcaatcatg cacgcacacg gtagacgcgc    1260
tgcgagcgga ggcggaaccc atccgtgtct gcccgcccgc cccgcagccg ccctcccaaa    1320
cgggacaagc cggggcggcc caaaacgagc aaggaaagca gcctcctact gtggcagccc    1380
gcccccacga ccaccatctc gccttccatt tccctggacg gaccagagcc gtcccgagcc    1440
gcccctgacc tagccaccca gcatttcctg tttcgtcccg cgccgccgtg acgtgaccga    1500
gaaaagcaaa agaggaaaaa gcgaaaatgc taaaggaaaa aactctgctc ttttattcct    1560
```

| | |
|---|---:|
| tctatatcta ctccagccta gggtacacac tatatatata tatatatata tatatatata | 1620 |
| tatatatata tatatatata tatatatata aaagtagaaa aaagaagaag aaaatgttgc | 1680 |
| tctactgctc tatggtgtgg gtttgtggcg agaaaaaatg atttggggaa agcaatatgg | 1740 |
| gggagattcg cgcgtacgat cgtccgcacac gtcgacacgg ggcgggcccg cggtggggca | 1800 |
| tcgtgtggct gcaggaccgc ggggccccgc ggcgcgggcc gggccaatgg gtgctcgaca | 1860 |
| gcggacatgc cccagaccag cccggtattg cataccgcgc tcggggccag atcccttaa | 1920 |
| aaccccctcc cgtcgccctg ccggaaccct catttggcca tccctctcc cctcccactt | 1980 |
| cacccaacca cctgacag | 1998 |

<210> SEQ ID NO 2
<211> LENGTH: 6276
<212> TYPE: DNA
<213> ORGANISM: Artificial Sequence
<220> FEATURE:
<223> OTHER INFORMATION: T-DNA

<400> SEQUENCE: 2

| | |
|---|---:|
| aattacaacg gtatatatcc tgccagtact gggcccctc gagggcgatc gctacgtacc | 60 |
| tgcaggcccg ggttaattaa gcggccgcct agttcccaat ttaagagtgg attatttgat | 120 |
| cacgggatca tctattccct ataaaacttt gagatgtttt ctatgaagta tggtttacac | 180 |
| agtatatctg atctaaatat tggttttgca ttcttggaaa cacactgcaa agtttaggga | 240 |
| tgctcatgtt tgtatctttt caatcataga gatatactcc ctccgtccgt caaaaactgt | 300 |
| gcatctaaca gtatattttt tttccataaa gagtgtacat ctacattttc tatgcgctta | 360 |
| gcttttaatt taaccggtat taagtgacta atgtagtaac ttgtgctcta gctattggct | 420 |
| gcatgcctaa ccttaattac tgcatgcagc aacgttcatt taatcttctt ttctcaatgg | 480 |
| ttgtatgtac acataagtct gttatttttg tacaataatt atgtcatgga ggtctttctt | 540 |
| ggtctatgtg caaatctctg tatgcacggt ttttggcgga cggagggagt acacgacata | 600 |
| ttcacaagca aaaagaaaa agttggacat ggcatattcg caaaaaaga ataagaaaa | 660 |
| gagaagagat gtgcatggca tgattgtgaa acctatcctc atcgatcgta aaaagcggta | 720 |
| ttggtatttt tagggaata aagagcgcta ttggtggttg ctggttacat cgaatggttg | 780 |
| caaagtggtc atttgacaag cacgcatgtg ggctttatct gtttgtcatc ataaacgata | 840 |
| aatgggtcaa gattcacaga tcagagaata cgtcgtcaaa gtctcgaaca cttcactgcg | 900 |
| tggtctactg ggcccaatag cagttttagt gaacaaacca ttttagtgct gcaatagttt | 960 |
| cagcacgatc ctttcctttg taccgagaag ccggtcaccg cagatatatc acatgcactt | 1020 |
| tccgcatttt tttaatatta tatcacatgc acagttctac aagacataca cagagcgttt | 1080 |
| atttttttg tgagaaggaa aacacatgag ccgtttcaac atcgcatgat tcgacgctgg | 1140 |
| gcaacagtgt attgatgggt ggaggactgg tcggcgcaca cgcgcgcaca gtaccctac | 1200 |
| tccggcggga gtatcttcca ttcattccag aaatacgcgg gtcggccaaa agtagaaaaa | 1260 |
| tacactgcgc cgacccaacc cacacgcagc aacggttcgc gtcaaaagtc cagctcgcgt | 1320 |
| caatcatgca cgcacacggt agacgcgctg cgagcggagg cggaacccat ccgtgtctgc | 1380 |
| ccgcccgccc cgcagccgcc ctcccaaacg ggacaagccg gggcggccca aaacgagcaa | 1440 |
| ggaaagcagc ctcctactgt ggcagcccgc ccccacgacc accatctcgc cttccatttc | 1500 |
| cctggacgga ccagagccgt cccgagccgc ccctgaccta gccacccagc atttcctgtt | 1560 |

-continued

```
tcgtcccgcg ccgccgtgac gtgaccgaga aaagcaaaag aggaaaaagc gaaaatgcta    1620
aaggaaaaaa ctctgctctt ttattccttc tatatctact ccagcctagg gtacacacta    1680
tatatatata tatatatata tatatatata tatatatata tatatatata tatatataaa    1740
agtagaaaaa agaagaagaa aatgttgctc tactgctcta tggtgtgggt ttgtggcgag    1800
aaaaaatgat ttgggggaaag caatatgggg gagattcgcg cgtacgatcg tccgacacgt    1860
cgacacgggg cgggccccgcg gtggggcatc gtgtggctgc aggaccgcgg ggccccgcgg    1920
cgcgggccgg gccaatgggt gctcgacagc ggacatgccc cagaccagcc cggtattgca    1980
taccgcgctc ggggccagat ccctttaaaa cccctcccg tcgccctgcc ggaaccctca    2040
tttggccatc ccctctcccc tcccacttca cccaaccacc tgacagacca tggtccgtcc    2100
tgtagaaacc ccaacccgtg aaatcaaaaa actcgacggc ctgtgggcat tcagtctgga    2160
tcgcgaaaac tgtggaattg atcagcgttg gtgggaaagc gcgttacaag aaagccgggc    2220
aattgctgtg ccaggcagtt ttaacgatca gttcgccgat gcagatattc gtaattatgc    2280
gggcaacgtc tggtatcagc gcgaagtctt tataccgaaa ggttgggcag ccagcgtat    2340
cgtgctgcgt ttcgatgcgg tcactcatta cggcaaagtg tgggtcaata atcaggaagt    2400
gatggagcat cagggcggct atacgccatt tgaagccgat gtcacgccgt atgttattgc    2460
cgggaaaagt gtacgtaagt ttctgcttct acctttgata tatatataat aattatcatt    2520
aattagtagt aatataatat ttcaaatatt tttttcaaaa taaaagaatg tagtatatag    2580
caattgcttt tctgtagttt ataagtgtgt atattttaat ttataacttt tctaatatat    2640
gaccaaaatt tgttgatgtg caggtatcac cgtttgtgtg aacaacgaac tgaactggca    2700
gactatcccg ccgggaatgg tgattaccga cgaaacggc aagaaaaagc agtcttactt    2760
ccatgatttc tttaactatg ccggaatcca tcgcagcgta atgctctaca ccacgccgaa    2820
cacctgggtg gacgatatca ccgtggtgac gcatgtcgcg caagactgta accacgcgtc    2880
tgttgactgg caggtggtgg ccaatggtga tgtcagcgtt gaactgcgtg atgcggatca    2940
acaggtggtt gcaactggac aaggcactag cgggactttg caagtggtga atccgcacct    3000
ctggcaaccg ggtgaaggtt atctctatga actgtgcgtc acagccaaaa gccagacaga    3060
gtgtgatatc tacccgcttc gcgtcggcat ccggtcagtg gcagtgaagg gcgaacagtt    3120
cctgattaac cacaaaccgt tctactttac tggctttggt cgtcatgaag atgcggactt    3180
gcgtggcaaa ggattcgata cgtgctgat ggtgcacgac cacgcattaa tggactggat    3240
tggggccaac tcctaccgta cctcgcatta cccttacgct gaagagatgc tcgactgggc    3300
agatgaacat ggcatcgtgg tgattgatga aactgctgct gtcggcttta acctctcttt    3360
aggcattggt ttcgaagcgg gcaacaagcc gaaagaactg tacagcgaag aggcagtcaa    3420
cggggaaact cagcaagcgc acttacaggc gattaaagag ctgatagcgc gtgacaaaaa    3480
ccacccaagc gtggtgatgt ggagtattgc caacgaaccg gatacccgtc cgcaaggtgc    3540
acgggaatat ttcgcgccac tggcggaagc aacgcgtaaa ctcgacccga cgcgtccgat    3600
cacctgcgtc aatgtaatgt tctgcgacgc tcacaccgat accatcagcg atctctttga    3660
tgtgctgtgc ctgaaccgtt attacggatg gtatgtccaa agcggcgatt tggaaacggc    3720
agagaaggta ctggaaaaag aacttctggc ctggcaggag aaactgcatc agccgattat    3780
catcaccgaa tacggcgtgg atacgttagc cgggctgcac tcaatgtaca ccgacatgtg    3840
gagtgaagag tatcagtgtg catggctgga tatgtatcac cgcgtctttg atcgcgtcag    3900
cgccgtcgtc ggtgaacagg tatggaattt cgccgatttt gcgacctcgc aaggcatatt    3960
```

-continued

```
gcgcgttggc ggtaacaaga aagggatctt cactcgcgac cgcaaaccga agtcggcggc    4020 tttttctgctg caaaaacgct ggactggcat gaacttcggt gaaaaaccgc agcagggagg    4080
caaacaatga atcaacaact ctcctggcgc accatcgtcg gctacagcct cggcgcgtgg    4140
cgcgccgaag cagatcgttc aaacatttgg caataaagtt tcttaagatt gaatcctgtt    4200
gccggtcttg cgatgattat catataattt ctgttgaatt acgttaagca tgtaataatt    4260
aacatgtaat gcatgacgtt atttatgaga tgggttttta tgattagagt cccgcaatta    4320
tacatttaat acgcgataga aaacaaaata tagcgcgcaa actaggataa attatcgcgc    4380
gcggtgtcat ctatgttact agatcggaat tcgatatcat taccctgtta tccctaaagc    4440
ttattaatat aacttcgtat agcatacatt atacgaagtt atgtttccta cgcagcaggt    4500
ctcatcaaga cgatctaccc gagtaacaat ctccaggaga tcaaatacct tcccaagaag    4560
gttaaagatg cagtcaaaag attcaggact aattgcatca agaacacaga gaaagacata    4620
tttctcaaga tcagaagtac tattccagta tggacgattc aaggcttgct tcataaacca    4680
aggcaagtaa tagagattgg agtctctaaa aaggtagttc ctactgaatc taaggccatg    4740
catggagtct aagattcaaa tcgaggatct aacagaactc gccgtgaaga ctggcgaaca    4800
gttcatacag agtctttac gactcaatga caagaagaaa atcttcgtca acatggtgga    4860
gcacgacact ctggtctact ccaaaaatgt caaagataca gtctcagaag accaaagggc    4920
tattgagact tttcaacaaa ggataatttc gggaaacctc ctcggattcc attgcccagc    4980
tatctgtcac ttcatcgaaa ggacagtaga aaaggaaggt ggctcctaca aatgccatca    5040
ttgcgataaa ggaaaggcta tcattcaaga tgcctctgcc gacagtggtc ccaaagatgg    5100 accccccaccc acgaggagca tcgtggaaaa agaagacgtt ccaaccacgt cttcaaagca    5160
agtggattga tgtgacatct ccactgacgt aagggatgac gcacaatccc actatccttc    5220
gcaagaccct tcctctatat aaggaagttc atttcatttg gagaggacac gctgaaatca    5280
ccagtctctc tctataaatc tatctctctc tctataacaa tggacccaga acgacgcccg    5340
gccgacatcc gccgtgccac cgaggcggac atgccggcgg tctgcaccat cgtcaaccac    5400
tacatcgaga caagcacggt caacttccgt accgagccgc aggaaccgca ggagtggacg    5460
gacgacctcg tccgtctgcg ggagcgctat ccctggctcg tcgccgaggt ggacggcgag    5520
gtcgccggca tcgcctacgc ggggccctgg aaggcacgca acgcctacga ctggacggcc    5580
gagtcgaccg tgtacgtctc ccccgccac cagcggacgg gactgggctc cacgctctac    5640
acccacctgc tgaagtccct ggaggcacag ggcttcaaga gcgtggtcgc tgtcatcggg    5700
ctgcccaacg acccgagcgt gcgcatgcac gaggcgctcg atatgccccc ccgcggcatg    5760 ctgcgggcg ccggcttcaa gcacgggaac tggcatgacg tgggtttctg gcagctggac    5820
ttcagcctgc cggtaccgcc ccgtccggtc ctgcccgtca ccgagatctg agatcacccg    5880
ttctaggatc cgaagcagat cgttcaaaca tttggcaata aagttttctta agattgaatc    5940 ctgttgccgg tcttgcgatg attatcatat aatttctgtt gaattacgtt aagcatgtaa    6000
taattaacat gtaatgcatg acgttattta tgagatgggt ttttatgatt agagtcccgc    6060
aattatacat ttaatacgcg atagaaaaca aaatatagcg cgcaaactag gataaattat    6120
cgcgcgcggt gtcatctatg ttactagatc gaaacataac ttcgtatagc atacattata    6180
cgaagttata tggatctcga ggcattacgg cattacggca ctcgcgaggg tcccaattcg    6240
agcatggagc catttacaat tgaatatatc ctgccg                              6276
```

ANTHER-SPECIFIC PROMOTER AND USES THEREOF

This application is a National Stage application of International Application No. PCT/EP2018/056537, filed Mar. 15, 2018, which claims priority to European Patent Application No. 17162487.7, filed on Mar. 23, 2017.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "181413_Seqlisting.txt", which was created on Sep. 5, 2019 and is 11,308 bytes in size. The subject matter of the Sequence Listing is incorporated herein in its entirety by reference.

FIELD OF THE INVENTION

The present invention relates to materials and methods for the expression of a gene of interest specifically in anthers of wheat plants. In particular, an expression cassette for regulating anther-specific expression in wheat plants is provided.

BACKGROUND

Modification of plants to alter and/or improve phenotypic characteristics (such as productivity or quality) requires the overexpression or down-regulation of endogenous genes or the expression of heterologous genes in plant tissues. Such genetic modification relies on the availability of a means to drive and to control gene expression as required. Indeed, genetic modification relies on the availability and use of suitable promoters which are effective in plants and which regulate gene expression so as to give the desired effect(s) in the transgenic plant.

For numerous applications in plant biotechnology a tissue-specific or a tissue-preferential expression profile is advantageous, since beneficial effects of expression in one tissue may have disadvantages in others.

Anther-specific promoters are useful for expressing or down-regulating genes specifically in the anthers to get the desired function or effect, such as creating a male sterile or restorer line for the production of hybrids or to spatially control the excision of the marker cassette when producing marker-free transgenic plants.

Examples of anther-specific promoters include the PAL3, PAL 4, CRP1 promoters from triticale and the CHSL1 promoter from wheat (Zaidi et al. 2016, Planta, doi:10.1007/s00425-016-2612-5), the OSIPP3 and OsLTP6 promoters from *Oryza sativa* (Manimaran et al. 2015, Plant Reprod 28:133-142; Liu et al. 2013, Planta, 238:845-857), PhLRR promoter from *Petunia hybrid* (Yue et al. 2014, Genetics and Molecular Research 13(4):9889-9898), and the PR10 promoter from *Lilium longiflorum* (Hsu et al. 2014, Plant Science, 215-216: 124-133).

There remains thus an interest in the isolation of novel anther-specific promoters for wheat. It is thus an objective of the present invention to provide a barley promoter having anther-specific activity in wheat. This objective is solved by the present invention as herein further explained.

SUMMARY

In one aspect, the invention provides a wheat plant cell or a wheat plant comprising a recombinant gene comprising (a) a nucleic acid having anther-specific promoter activity selected from the group consisting of (i) a nucleic acid comprising a nucleotide sequence of SEQ ID NO: 1 or a functional fragment thereof comprising the nucleotide sequence of SEQ ID NO: 1 from nucleotide position 1647 to nucleotide position 1947; (ii) a nucleic acid comprising a nucleotide sequence having at least about 95% sequence identity to SEQ ID NO: 1, or a functional fragment thereof, wherein said functional fragment comprises at least about 300 consecutive nucleotides upstream of the transcription start of SEQ ID NO: 1, operably linked to (b) a heterologous nucleic acid sequence encoding an expression product of interest, and optionally (c) a transcription termination and polyadenylation sequence, preferably a transcription termination and polyadenylation region functional in plants. In a further embodiment, said expression product of interest is an RNA capable of modulating the expression of a gene or is a protein.

A further embodiment provides seeds obtainable from the plant according to the invention.

Another embodiment provides a method of producing a transgenic wheat plant comprising the steps of (a) introducing or providing the recombinant gene described herein to a wheat plant cell to create transgenic cells; and (b) regenerating transgenic wheat plants from said transgenic cell.

Further provided is a method of effecting anther-specific expression of a nucleic acid in wheat comprising introducing the recombinant gene described herein into the genome of a wheat plant, or providing the wheat plant according to the invention. Also provided are methods for controlling pollination of a wheat plant, for controlling the excision of a marker in the production of marker-free transgenic wheat plants or for producing a commercially relevant product in a wheat plant, said methods comprising introducing the recombinant gene described herein into the genome of a wheat plant, or providing the wheat plant according to the invention.

Also provided is the use of the isolated nucleic acid having anther-specific promoter activity described herein to regulate expression of an operably linked nucleic acid in a plant, and the use of the isolated nucleic acid having anther-specific promoter activity described herein, or the recombinant gene described herein to control pollination of a wheat plant, to control the excision of a marker in the production of marker-free transgenic wheat plants or to produce a commercially relevant product in a wheat plant.

Yet another embodiment provides a method of producing food, feed, or an industrial product comprising (a) obtaining the plant or a part thereof, according to the invention; and (b) preparing the food, feed or industrial product from the plant or part thereof. In another embodiment, said food or feed is meal, grain, starch, flour or protein, or said industrial product is biofuel, industrial chemicals, a pharmaceutical or a nutraceutical.

BRIEF DESCRIPTION OF THE DRAWINGS

FIG. 1: GUS staining in wheat plants carrying Pvrn1Hv:: GUS. A: Developing spike; B and C: cross section through florets showing the anthers (Ps: pollen sac; F: filament) and the gynoecium (O: ovary) (B: control; C: stained tissues).

DETAILED DESCRIPTION

The present invention is based on the unexpected observation that SEQ ID NO: 1 has anther-specific promoter activity in wheat.

SEQ ID NO: 1 depicts the region upstream (i.e. located 5' upstream of) from the first ATG start codon of the VRN1 gene from *Hordeum vulgaris* (barley, VRN1 Hv). Such a promoter region may be at least about 350 bp, at least about 400 bp, at least about 500 bp, at least about 600 bp, at least about 700 bp, at least about 800 bp, at least about 900 bp, at least about 1000 bp, at least about 1100 bp, at least about 1200 bp, at least about 1300 bp, at least about 1400 bp, at least about 1500 bp, at least about 1600 bp, at least about 1700 bp, at least about 1800 bp, at least about 1900 bp, or at least about 2000 bp upstream of the first ATG start codon of the VRN1 Hv transcript. Such a promoter region may also be at least about 300 bp, at least about 400 bp, at least about 500 bp, at least about 600 bp, at least about 700 bp, at least about 800 bp, at least about 900 bp, at least about 1000 bp, at least about 1100 bp, at least about 1200 bp, at least about 1300 bp, at least about 1400 bp, at least about 1500 bp, at least about 1600 bp, at least about 1700 bp, at least about 1800 bp, at least about 1900 bp, or at least about 1950 bp upstream of the transcription start site.

VRN1 Hv is the VERNALIZATION1 gene from barley encoding a MADS box transcription factor required for the transition from vegetative growth to flowering after a period of cold called vernalization. As such the VRN1 gene expression pattern and its promoter activity have been described for example in Alonso-Peral et al. 2011 PLOS One, 6:e29456 as limited to leaves and shoot-apex after cold treatment in barley.

In one aspect, the invention provides a wheat plant cell or a wheat plant comprising a recombinant gene comprising (a) a nucleic acid having anther-specific promoter activity selected from the group consisting of (i) a nucleic acid comprising a nucleotide sequence of SEQ ID NO: 1 or a functional fragment thereof comprising the nucleotide sequence of SEQ ID NO: 1 from nucleotide position 1647 to nucleotide position 1947; (ii) a nucleic acid comprising a nucleotide sequence having at least about 95% sequence identity to SEQ ID NO: 1, or a functional fragment thereof, wherein said functional fragment comprises at least about 300 consecutive nucleotides upstream of the transcription start of SEQ ID NO: 1, operably linked to (b) a heterologous nucleic acid sequence encoding an expression product of interest, and optionally (c) a transcription termination and polyadenylation sequence, preferably a transcription termination and polyadenylation region functional in plants. In a further embodiment, said expression product of interest is an RNA capable of modulating the expression of a gene or is a protein.

The nucleic acid having anther-specific promoter activity described herein may also be comprised in a larger DNA molecule.

"Anther-specific promoter activity" in the context of this invention means the promoter activity is at least 10 times, or at least 20 times, or at least 50 times, or at least 100 times, or at least 200 times, or at least 500 times, or even at least 1000 times higher in anthers than in other tissues. In other words, in anther-specific promoter activity, transcription of the nucleic acid operably linked to the promoter described in the anthers is at least 10 times, or at least 20 times, or at least 50 times, or at least 100 times, or at least 200 times, or at least 500 times or even at least 1000 times higher than in other tissues. In other words, the anther-specific promoter drives anther-specific expression of the nucleic acid operably linked to the anther-specific promoter.

"Anther-specific promoter activity" encompasses "pollen sac-specific promoter activity".

"Pollen sac-specific promoter activity" in the context of this invention means the promoter activity is at least 10 times, or at least 20 times, or at least 50 times, or at least 100 times, or at least 200 times, or at least 500 times, or even at least 1000 times higher in pollen sac tissues than in other tissues. In other words, in pollen sac-specific promoter activity, transcription of the nucleic acid operably linked to the promoter described in the pollen sac is at least 10 times, or at least 20 times, or at least 50 times, or at least 100 times, or at least 200 times, or at least 500 times or even at least 1000 times higher than in other tissues. In other words, the pollen sac-specific promoter drives pollen sac-specific expression of the nucleic acid operably linked to the pollen sac-specific promoter.

The phrase "operably linked" refers to the functional spatial arrangement of two or more nucleic acid regions or nucleic acid sequences. For example, a promoter region may be positioned relative to a nucleic acid sequence such that transcription of a nucleic acid sequence is directed by the promoter region. Thus, a promoter region is "operably linked" to the nucleic acid sequence. "Functionally linked" is an equivalent term.

The phrases "DNA", "DNA sequence," "nucleic acid sequence," "nucleic acid molecule" "nucleotide sequence" and "nucleic acid" refer to a physical structure comprising an orderly arrangement of nucleotides. The DNA sequence or nucleotide sequence may be contained within a larger nucleotide molecule, vector, or the like. In addition, the orderly arrangement of nucleic acids in these sequences may be depicted in the form of a sequence listing, figure, table, electronic medium, or the like.

As used herein, "promoter" means a region of DNA sequence that is essential for the initiation of transcription of DNA, resulting in the generation of an RNA molecule that is complementary to the transcribed DNA; this region may also be referred to as a "5' regulatory region". Promoters are usually located upstream of the coding sequence to be transcribed and have regions that act as binding sites for RNA polymerase II and other proteins such as transcription factors (trans-acting protein factors that regulate transcription) to initiate transcription of an operably linked gene. Promoters may themselves contain sub-elements (i.e. promoter motifs) such as cis-elements or enhancer domains that regulate the transcription of operably linked genes. The promoters described herein may be altered to contain "enhancer DNA" to assist in elevating gene expression. As is known in the art, certain DNA elements can be used to enhance the transcription of DNA. These enhancers often are found 5' to the start of transcription in a promoter that functions in eukaryotic cells, but can often be inserted upstream (5') or downstream (3') to the coding sequence. In some instances, these 5' enhancer DNA elements are introns. Among the introns that are useful as enhancer DNA are the 5' introns from the rice actin 1 gene (see U.S. Pat. No. 5,641,876), the rice actin 2 gene, the maize alcohol dehydrogenase gene, the maize heat shock protein 70 gene (see U.S. Pat. No. 5,593,874), the maize shrunken 1 gene, the light sensitive 1 gene of *Solanum tuberosum*, the Arabidopsis histon 4 intron and the heat shock protein 70 gene of *Petunia hybrida* (see U.S. Pat. No. 5,659,122). Thus, as contemplated herein, a promoter or promoter region includes variations of promoters derived by inserting or deleting regulatory regions, subjecting the promoter to random or site-directed mutagenesis, etc. The activity or strength of a promoter may be measured in terms of the amounts of RNA it produces, or the amount of protein accumulation in a cell or tissue, relative to a promoter whose transcriptional activity has been previously assessed or relative to a promoter driving the expression of a housekeeping gene. A promoter as used herein may thus include sequences downstream of the transcription start, such as sequences coding the 5' untranslated region (5' UTR) of the RNA, introns located downstream of the transcription start, or even sequences encoding the protein.

A functional promoter fragment according to the invention may comprise the nucleotide sequence of SEQ ID NO: 1 from the nucleotide at position 1647 to the nucleotide at position 1947, or the nucleotide sequence of SEQ ID NO: 1 from the nucleotide at position 1547 to the nucleotide at position 1947, or the nucleotide sequence of SEQ ID NO: 1 from the nucleotide at position 1447 to the nucleotide at position 1947, or the nucleotide sequence of SEQ ID NO: 1 from the nucleotide at position 1347 to the nucleotide at position 1947, or the nucleotide sequence of SEQ ID NO: 1 from the nucleotide at position 1247 to the nucleotide at position 1947, or the nucleotide sequence of SEQ ID NO: 1 from the nucleotide at position 1147 to the nucleotide at position 1947, or the nucleotide sequence of SEQ ID NO: 1 from the nucleotide at position 1047 to the nucleotide at position 1947, or the nucleotide sequence of SEQ ID NO: 1 from the nucleotide at position 947 to the nucleotide at position 1947, or the nucleotide sequence of SEQ ID NO: 1 from the nucleotide at position 847 to the nucleotide at position 1947, or the nucleotide sequence of SEQ ID NO: 1 from the nucleotide at position 747 to the nucleotide at position 1947, or the nucleotide sequence of SEQ ID NO: 1 from the nucleotide at position 647 to the nucleotide at position 1947, or the nucleotide sequence of SEQ ID NO: 1 from the nucleotide at position 547 to the nucleotide at position 1947, or the nucleotide sequence of SEQ ID NO: 1 from the nucleotide at position 447 to the nucleotide at position 1947, or the nucleotide sequence of SEQ ID NO: 1 from the nucleotide at position 347 to the nucleotide at position 1947, or the nucleotide sequence of SEQ ID NO: 1 from the nucleotide at position 247 to the nucleotide at position 1947, or the nucleotide sequence of SEQ ID NO: 1 from the nucleotide at position 147 to the nucleotide at position 1947, or the nucleotide sequence of SEQ ID NO: 1 from the nucleotide at position 47 to the nucleotide at position 1947, or the nucleotide sequence of SEQ ID NO: 1 from the nucleotide at position 1 to the nucleotide at position 1947, or the nucleotide sequence of SEQ ID NO: 1 from the nucleotide at position 1647 to the nucleotide at position 1998, or the nucleotide sequence of SEQ ID NO: 1 from the nucleotide at position 1598 to the nucleotide at position 1998, or the nucleotide sequence of SEQ ID NO: 1 from the nucleotide at position 1498 to the nucleotide at position 1998, or the nucleotide sequence of SEQ ID NO: 1 from the nucleotide at position 1398 to the nucleotide at position 1998, or the nucleotide sequence of SEQ ID NO: 1 from the nucleotide at position 1298 to the nucleotide at position 1998, or the nucleotide sequence of SEQ ID NO: 1 from the nucleotide at position 1198 to the nucleotide at position 1998, or the nucleotide sequence of SEQ ID NO: 1 from the nucleotide at position 1098 to the nucleotide at position 1998, or the nucleotide sequence of SEQ ID NO: 1 from the nucleotide at position 998 to the nucleotide at position 1998, or the nucleotide sequence of SEQ ID NO: 1 from the nucleotide at position 898 to the nucleotide at position 1998, or the nucleotide sequence of SEQ ID NO: 1 from the nucleotide at position 798 to the nucleotide at position 1998, or the nucleotide sequence of SEQ ID NO: 1 from the nucleotide at position 698 to the nucleotide at position 1998, or the nucleotide sequence of SEQ ID NO: 1 from the nucleotide at position 598 to the nucleotide at position 1998, or the nucleotide sequence of SEQ ID NO: 1 from the nucleotide at position 498 to the nucleotide at position 1998, or the nucleotide sequence of SEQ ID NO: 1 from the nucleotide at position 398 to the nucleotide at position 1998, or the nucleotide sequence of SEQ ID NO: 1 from the nucleotide at position 298 to the nucleotide at position 1998, or the nucleotide sequence of SEQ ID NO: 1 from the nucleotide at position 198 to the nucleotide at position 1998, or the nucleotide sequence of SEQ ID NO: 1 from the nucleotide at position 98 to the nucleotide at position 1998, or the nucleotide sequence of SEQ ID NO: 1 from the nucleotide at position 1 to the nucleotide at position 1998.

Promoter activity of a functional promoter fragment in anthers may be determined by those skilled in the art, for example using analysis of RNA accumulation produced from the nucleic acid which is operably linked to the promoter as described herein or a functional fragment thereof, whereby the nucleic acid which is operably linked to the promoter can be the nucleic acid which is naturally linked to the promoter, i.e. the endogenous gene of which expression is driven by the promoter.

The anther-specific expression capacity of the identified or generated fragments of the promoter described herein can be conveniently tested by determining levels of the transcript of which expression is naturally driven by the promoter described herein, i.e. endogenous transcript levels, such as, for example, using the methods as described herein in the Examples. Further, the anther-specific expression capacity of the identified or generated fragments of the promoter described herein can be conveniently tested by operably linking such DNA molecules to a nucleotide sequence encoding an easy scorable marker, e.g. a beta-glucuronidase gene, introducing such a chimeric gene into a plant and analyzing the expression pattern of the marker in anthers as compared with the expression pattern of the marker in other parts of the plant. Other candidates for a marker (or a reporter gene) are chloramphenicol acetyl transferase (CAT) and proteins with fluorescent properties, such as green fluorescent protein (GFP) from *Aequora victoria*, or proteins with luminescent properties such as the *Renilla* luciferase or the bacterial lux operon. To define a minimal promoter region, a DNA segment representing the promoter region is removed from the 5' region of the gene of interest and operably linked to the coding sequence of a marker (reporter) gene by recombinant DNA techniques well known to the art. The reporter gene is operably linked downstream of the promoter, so that transcripts initiating at the promoter proceed through the reporter gene. Reporter genes generally encode proteins, which are easily measured, including, but not limited to, chloramphenicol acetyl transferase (CAT), beta-glucuronidase (GUS), green fluorescent protein (GFP), beta-galactosidase (beta-GAL), and luciferase. The expression cassette containing the reporter gene under the control of the promoter can be introduced into an appropriate cell type by transfection techniques well known to the art. To assay for the reporter protein, cell lysates are prepared and appropriate assays, which are well known in the art, for the reporter protein are performed. For example, if CAT were the reporter gene of choice, the lysates from cells transfected with constructs containing CAT under the control of a promoter under study are mixed with isotopically labeled chloramphenicol and acetyl-coenzyme A (acetyl-CoA). The CAT enzyme transfers the acetyl group from acetyl-CoA to the 2- or 3-position of chloramphenicol. The reaction is monitored by thin-layer chromatography, which separates acetylated chloramphenicol from unreacted material. The reaction products are then visualized by autoradiography. The level of enzyme activity corresponds to the amount of enzyme that was made, which in turn reveals the level of expression and the early stage seed-specific and endosperm preferential functionality from the promoter or promoter fragment of interest. This level of expression can also be compared to other promoters to determine the relative strength of the promoter under study. Once activity and functionality is confirmed, additional mutational and/or deletion analyses may be employed to determine the minimal region and/or sequences required to initiate transcription. Thus, sequences can be deleted at the 5' end of the promoter region and/or at the 3' end of the promoter region, and nucleotide substitutions introduced. These constructs are then again introduced in cells and their activity and/or functionality determined.

The activity or strength of a promoter may be measured in terms of the amount of mRNA or protein accumulation it specifically produces, relative to the total amount of mRNA or protein. The promoter preferably expresses an operably linked nucleic acid sequence at a level greater than about 0.01%, about 0.02%, more preferably greater than about 0.05% of the total mRNA. Alternatively, the activity or strength of a promoter may be expressed relative to a well-characterized promoter (for which transcriptional activity was previously assessed).

Suitable to the invention are nucleic acids comprising anther-specific promoter activity which comprise a nucleotide sequence having at least 40%, at least 50%, or at least 60%, or at least 70%, or at least 80%, or at least 85%, or at least 90%, or at least 95%, or at least 98% sequence identity to the herein described promoters and promoter regions or functional fragments thereof and are also referred to as variants. The term "variant" with respect to the transcription regulating nucleotide sequences SEQ ID NO: 1 of the invention is intended to mean substantially similar sequences. Naturally occurring allelic variants such as these can be identified with the use of well-known molecular biology techniques, as, for example, with polymerase chain reaction (PCR) as herein outlined before. Variant nucleotide sequences also include synthetically derived nucleotide sequences, such as those generated, for example, by using site-directed mutagenesis of any one of SEQ ID NO: 1. Generally, nucleotide sequence variants of the invention will have at least 40%, 50%, 60%, to 70%, e.g., preferably 71%, 72%, 73%, 74%, 75%, 76%, 77%, 78%, to 79%, generally at least 80%, e.g., 81% to 84%, at least 85%, e.g., 86%, 87%, 88%, 89%, 90%, 91%, 92%, 93%, 94%, 95%, 96%, 97%, to 98% and 99% nucleotide sequence identity to the native (wild type or endogenous) nucleotide sequence or a functional fragment thereof. Derivatives of the DNA molecules disclosed herein may include, but are not limited to, deletions of sequence, single or multiple point mutations, alterations at a particular restriction enzyme site, addition of functional elements, or other means of molecular modification which may enhance, or otherwise alter promoter expression. Techniques for obtaining such derivatives are well-known in the art (see, for example, J. F. Sambrook, D. W. Russell, and N. Irwin (2000) Molecular Cloning: A Laboratory Manual, 3$^{rd}$ edition Volumes 1, 2, and 3. Cold Spring Harbor Laboratory Press). For example, one of ordinary skill in the art may delimit the functional elements within the promoters disclosed herein and delete any non-essential elements. Functional elements may be modified or combined to increase the utility or expression of the sequences of the invention for any particular application. Those of skill in the art are familiar with the standard resource materials that describe specific conditions and procedures for the construction, manipulation, and isolation of macromolecules (e.g., DNA molecules, plasmids, etc.), as well as the generation of recombinant organisms and the screening and isolation of DNA molecules. As used herein, the term "percent sequence identity" refers to the percentage of identical nucleotides between two segments of a window of optimally aligned DNA. Optimal alignment of sequences for aligning a comparison window are well-known to those skilled in the art and may be conducted by tools such as the local homology algorithm of Smith and Waterman (Waterman, M. S. Introduction to Computational Biology: Maps, sequences and genomes. Chapman & Hall. London (1995), the homology alignment algorithm of Needleman and Wunsch (J. Mol. Biol., 48:443-453 (1970), the search for similarity method of Pearson and Lipman (Proc. Natl. Acad. Sci., 85:2444 (1988), and preferably by computerized implementations of these algorithms such as GAP, BESTFIT, FASTA, and TFASTA available as part of the GCG (Registered Trade Mark), Wisconsin Package (Registered Trade Mark from Accelrys Inc., San Diego, Calif.). An "identity fraction" for aligned segments of a test sequence and a reference sequence is the number of identical components that are shared by the two aligned sequences divided by the total number of components in the reference sequence segment, i.e., the entire reference sequence or a smaller defined part of the reference sequence. Percent sequence identity is represented as the identity fraction times 100. The comparison of one or more DNA sequences may be to a full-length DNA sequence or a portion thereof, or to a longer DNA sequence.

A nucleic acid comprising a nucleotide sequence having at least 95% sequence identity to SEQ ID NO: 1 can thus be a nucleic acid comprising a nucleotide sequence having at least 95%, or at least 96%, or at least 97%, or at least 98%, or at least 99%, or 100% sequence identity to SEQ ID NO: 1.

A "functional fragment" of a nucleic acid comprising anther-specific promoter denotes a nucleic acid comprising a stretch of the nucleic acid sequences of SEQ ID NO: 1, or of the nucleic acid having at least 95% sequence identity to SEQ ID NO: 1 which still exerts the desired function, i.e. which has anther-specific promoter activity. Assays for determining anther-specific promoter activity are provided herein. Preferably, the functional fragment of the anther-specific promoter contains the conserved promoter motifs, such as, for example, conserved promoter motifs as described in DoOP (doop.abc.hu, databases of Orthologous Promoters, Barta E. et al (2005) Nucleic Acids Research Vol. 33, D86-D90). A functional fragment may be a fragment of at least about 350 bp, at least about 400 bp, at least about 500 bp, at least about 600 bp, at least about 700 bp, at least about 800 bp, at least about 900 bp, at least about 1000 bp, at least about 1100 bp, at least about 1200 bp, at least about 1300 bp, at least about 1400 bp, at least about 1500 bp, at least about 1600 bp, at least about 1700 bp, at least about 1800 bp, at least about 1900 bp from the translation start site. A functional fragment may be a fragment of at least about 300 bp, at least about 400 bp, at least about 500 bp, at least about 600 bp, at least about 700 bp, at least about 800 bp, at least about 900 bp, at least about 1000 bp, at least about 1100 bp, at least about 1200 bp, at least about 1300 bp, at least about 1400 bp, at least about 1500 bp, at least about 1600 bp, at least about 1700 bp, at least about 1800 bp, at least about 1900 bp from the transcription start site.

A nucleic acid comprising the nucleotide sequence of SEQ ID NO: 1 which further comprises insertion, deletion, substitution of at least 1 nucleotide up to 20 nucleotides, at least 1 nucleotide up to 15 nucleotides, at least 1 nucleotide up to 10 nucleotides, at least 1 nucleotide up to 5 nucleotides, at least 1 nucleotide up to 4 nucleotides, at least 1 nucleotide up to 3 nucleotides, or even at least 1 nucleotide up to 2 nucleotides may cover at least about 350 bp, at least about 400 bp, at least about 500 bp, at least about 600 bp, at least about 700 bp, at least about 800 bp, at least about 900 bp, at least about 1000 bp, at least about 1100 bp, at least about 1200 bp, at least about 1300 bp, at least about 1400 bp, at least about 1500 bp, at least about 1600 bp, at least about 1700 bp, at least about 1800 bp, at least about 1900 bp, at least about 2000 bp from the translation start site. A nucleic acid comprising the nucleotide sequence of SEQ ID NO: 1 which further comprises insertion, deletion, substitution of at least 1 nucleotide up to 20 nucleotides, at least 1 nucleotide up to 15 nucleotides, at least 1 nucleotide up to 10 nucleotides, at least 1 nucleotide up to 5 nucleotides, at least 1 nucleotide up to 4 nucleotides, at least 1 nucleotide up to 3 nucleotides, or even at least 1 nucleotide up to 2 nucleotides may also cover at least about 300 bp, at least about 400 bp, at least about 500 bp, at least about 600 bp, at least about 700 bp, at least about 800 bp, at least about 900 bp, at least about 1000 bp, at least about 1100 bp, at least about 1200 bp, at least about 1300 bp, at least about 1400 bp, at least about 1500 bp, at least about 1600 bp, at least about 1700 bp, at least about 1800 bp, at least about 1900 bp, at least about 1950 bp from the transcription start site.

A shorter promoter functional fragment was identified on the promoter sequence disclosed herein.

Variants of the promoter described herein include those which comprise the identified shorter promoter—from nucleotide position 1647 to nucleotide position 1947—but have otherwise been modified to delete nucleotide stretches within the sequence which are not needed for the promoter to be functional in anther-specific manner. For example, any nucleotide stretch located outside of the minimum promoter fragment may be at least partially deleted to result in a shorter nucleotide sequence than the about 2 kb sequence of SEQ ID NO: 1.

"Isolated nucleic acid", used interchangeably with "isolated DNA" as used herein refers to a nucleic acid not occurring in its natural genomic context, irrespective of its length and sequence. Isolated DNA can, for example, refer to DNA which is physically separated from the genomic context, such as a fragment of genomic DNA. Isolated DNA can also be an artificially produced DNA, such as a chemically synthesized DNA, or such as DNA produced via amplification reactions, such as polymerase chain reaction (PCR) well-known in the art. Isolated DNA can further refer to DNA present in a context of DNA in which it does not occur naturally. For example, isolated DNA can refer to a piece of DNA present in a plasmid. Further, the isolated DNA can refer to a piece of DNA present in another chromosomal context than the context in which it occurs naturally, such as for example at another position in the genome than the natural position, in the genome of another species than the species in which it occurs naturally, or in an artificial chromosome.

The term "expression product" refers to a product of transcription. Said expression product can be the transcribed RNA. It is understood that the RNA which is produced is a biologically active RNA. Said expression product can also be a peptide, a polypeptide, or a protein, when said biologically active RNA is an mRNA and said protein is produced by translation of said mRNA.

Alternatively, the heterologous nucleic acid, operably linked to the promoter described herein, may also code for an RNA capable of modulating the expression of a gene. Said RNA capable of modulating the expression of a gene can be an RNA which reduces expression of a gene. Said RNA can reduce the expression of a gene for example through the mechanism of RNA-mediated gene silencing.

Said RNA capable of modulating the expression of a gene can be a silencing RNA down-regulating expression of a target gene. As used herein, "silencing RNA" or "silencing RNA molecule" refers to any RNA molecule, which upon introduction into a plant cell, reduces the expression of a target gene. Such silencing RNA may e.g. be so-called "antisense RNA", whereby the RNA molecule comprises a sequence of at least 20 consecutive nucleotides having 95% sequence identity to the complement of the sequence of the target nucleic acid, preferably the coding sequence of the target gene. However, antisense RNA may also be directed to regulatory sequences of target genes, including the promoter sequences and transcription termination and polyadenylation signals. Silencing RNA further includes so-called "sense RNA" whereby the RNA molecule comprises a sequence of at least 20 consecutive nucleotides having 95% sequence identity to the sequence of the target nucleic acid. Other silencing RNA may be "unpolyadenylated RNA" comprising at least 20 consecutive nucleotides having 95% sequence identity to the complement of the sequence of the target nucleic acid, such as described in WO01/12824 or U.S. Pat. No. 6,423,885 (both documents herein incorporated by reference). Yet another type of silencing RNA is an RNA molecule as described in WO03/076619 (herein incorporated by reference) comprising at least 20 consecutive nucleotides having 95% sequence identity to the sequence of the target nucleic acid or the complement thereof, and further comprising a largely-double stranded region as described in WO03/076619 (including largely double stranded regions comprising a nuclear localization signal from a viroid of the Potato spindle tuber viroid-type or comprising CUG trinucleotide repeats). Silencing RNA may also be double stranded RNA comprising a sense and antisense strand as herein defined, wherein the sense and antisense strand are capable of base-pairing with each other to form a double stranded RNA region (preferably the said at least 20 consecutive nucleotides of the sense and antisense RNA are complementary to each other). The sense and antisense region may also be present within one RNA molecule such that a hairpin RNA (hpRNA) can be formed when the sense and antisense region form a double stranded RNA region. hpRNA is well-known within the art (see e.g WO99/53050, herein incorporated by reference). The hpRNA may be classified as long hpRNA, having long, sense and antisense regions which can be largely complementary, but need not be entirely complementary (typically larger than about 200 bp, ranging between 200-1000 bp). hpRNA can also be rather small ranging in size from about 30 to about 42 bp, but not much longer than 94 bp (see WO04/073390, herein incorporated by reference). Silencing RNA may also be artificial micro-RNA molecules as described e.g. in WO2005/052170, WO2005/047505 or US 2005/0144667, or ta-siRNAs as described in WO2006/074400 (all documents incorporated herein by reference). Said RNA capable of modulating the expression of a gene can also be an RNA ribozyme.

The nucleic acid sequence heterologous to the promoter described herein may generally be any nucleic acid sequence effecting increased, altered (e.g. in a different organ) or reduced level of transcription of a gene for which such expression modulation is desired. The nucleic acid sequence can for example encode a protein of interest. Exemplary genes for which an increased or reduced level of transcription may be desired in the anthers are e.g. nucleic acids that can selectively disrupt the metabolism, functioning, and/or development of stamen cells of the plant.

A "transcription termination and polyadenylation region" as used herein is a sequence that drives the cleavage of the nascent RNA, whereafter a poly(A) tail is added at the resulting RNA 3' end, functional in plant cells. Transcription termination and polyadenylation signals functional in plant cells include, but are not limited to, 3'nos, 3'35S, 3'his and 3'g7.

The term "protein" interchangeably used with the term "polypeptide" as used herein describes a group of molecules consisting of more than 30 amino acids, whereas the term "peptide" describes molecules consisting of up to 30 amino acids. Proteins and peptides may further form dimers, trimers and higher oligomers, i.e. consisting of more than one (poly)peptide molecule. Protein or peptide molecules forming such dimers, trimers etc. may be identical or non-identical. The corresponding higher order structures are, consequently, termed homo- or heterodimers, homo- or heterotrimers etc. The terms "protein" and "peptide" also refer to naturally modified proteins or peptides wherein the modification is effected e.g. by glycosylation, acetylation, phosphorylation and the like. Such modifications are well known in the art.

The term "heterologous" refers to the relationship between two or more nucleic acid or protein sequences that are derived from different sources. For example, a promoter is heterologous with respect to an operably linked DNA region, such as a coding sequence if such a combination is not normally found in nature. In addition, a particular sequence may be "heterologous" with respect to a cell or organism into which it is inserted (i.e. does not naturally occur in that particular cell or organism).

The term "recombinant gene" refers to any gene that contains: a) DNA sequences, including regulatory and coding sequences that are not found together in nature, or b) sequences encoding parts of proteins not naturally adjoined, or c) parts of promoters that are not naturally adjoined. Accordingly, a recombinant gene may comprise regulatory sequences and coding sequences that are derived from different sources, or comprise regulatory sequences, and coding sequences derived from the same source, but arranged in a manner different from that found in nature.

Any of the promoters and heterologous nucleic acid sequences described herein may be provided in a recombinant vector. A recombinant vector typically comprises, in a 5' to 3' orientation: a promoter to direct the transcription of a nucleic acid sequence and a nucleic acid sequence. The recombinant vector may further comprise a 3' transcriptional terminator, a 3' polyadenylation signal, other untranslated nucleic acid sequences, transit and targeting nucleic acid sequences, selectable markers, enhancers, and operators, as desired. The wording "5' UTR" refers to the untranslated region of DNA upstream, or 5' of the coding region of a gene and "3' UTR" refers to the untranslated region of DNA downstream, or 3' of the coding region of a gene. Means for preparing recombinant vectors are well known in the art. Methods for making recombinant vectors particularly suited to plant transformation are described in U.S. Pat. Nos. 4,971,908, 4,940,835, 4,769,061 and 4,757,011. Typical vectors useful for expression of nucleic acids in higher plants are well known in the art and include vectors derived from the tumor-inducing (Ti) plasmid of *Agrobacterium tumefaciens*. One or more additional promoters may also be provided in the recombinant vector. These promoters may be operably linked, for example, without limitation, to any of the nucleic acid sequences described herein. Alternatively, the promoters may be operably linked to other nucleic acid sequences, such as those encoding transit peptides, selectable marker proteins, or antisense sequences. These additional promoters may be selected on the basis of the cell type into which the vector will be inserted. Also, promoters which function in bacteria, yeast, and plants are all well taught in the art. The additional promoters may also be selected on the basis of their regulatory features. Examples of such features include enhancement of transcriptional activity, inducibility, tissue specificity, and developmental stage-specificity.

The recombinant vector may also contain one or more additional nucleic acid sequences. These additional nucleic acid sequences may generally be any sequences suitable for use in a recombinant vector. Such nucleic acid sequences include, without limitation, any of the nucleic acid sequences, and modified forms thereof, described above. The additional structural nucleic acid sequences may also be operably linked to any of the above described promoters. The one or more structural nucleic acid sequences may each be operably linked to separate promoters. Alternatively, the structural nucleic acid sequences may be operably linked to a single promoter (i.e., a single operon).

Other nucleic acid sequences may also be introduced into the wheat plant cell along with the promoter and structural nucleic acid sequence, e. g. also in connection with the vector described herein. These other sequences may include 3' transcriptional terminators, 3' polyadenylation signals, other untranslated nucleic acid sequences, transit or targeting sequences, selectable markers, enhancers, and operators. Preferred nucleic acid sequences of the present invention, including recombinant vectors, structural nucleic acid sequences, promoters, and other regulatory elements, are described above.

Yet a further embodiment provides seeds obtainable from the plant according to the invention.

The wheat plant cell or wheat plant according to the invention can be a wheat plant cell or a wheat plant comprising a recombinant gene of which either the promoter, or the promoter and the heterologous nucleic acid sequence operably linked to said promoter, are heterologous with respect to the plant cell. Such plant cells or plants may be transgenic plant in which the recombinant gene is introduced via transformation. The promoter according to the invention can be integrated in a targeted manner in the genome of the plant or plant cell upstream of an endogenous nucleic acid encoding an expression product of interest, i.e. to modulate the expression pattern of an endogenous gene. Said promoter and/or said heterologous nucleic acid can be integrated in a targeted manner in the plant genome via targeted sequence insertion, using, for example, the methods as described in WO2005/049842.

Yet another embodiment provides a method of producing a transgenic wheat plant comprising the steps of (a) introducing or providing the recombinant gene described herein to a wheat plant cell to create transgenic cells; and (b) regenerating transgenic plants from said transgenic cell.

"Introducing" in connection with the present application relates to the placing of genetic information in a plant cell or plant by artificial means. This can be effected by any method known in the art for introducing RNA or DNA into plant cells, protoplasts, calli, roots, tubers, seeds, stems, leaves, seedlings, embryos, pollen and microspores, other plant tissues, or whole plants. "Introducing" also comprises stably integrating into the plant's genome. Introducing the recombinant gene can be performed by transformation.

The term "transformation" herein refers to the introduction (or transfer) of nucleic acid into a recipient host such as a plant or any plant parts or tissues including plant cells, protoplasts, calli, roots, tubers, seeds, stems, leaves, seedlings, embryos and pollen. Plants containing the transformed nucleic acid sequence are referred to as "transgenic plants". Transformed, transgenic and recombinant refer to a host organism such as a plant into which a heterologous nucleic acid molecule (e.g. an expression cassette or a recombinant vector) has been introduced. The nucleic acid can be stably integrated into the genome of the plant.

As used herein, the phrase "transgenic plant" refers to a plant having an introduced nucleic acid stably introduced into a genome of the plant, for example, the nuclear or plastid genomes. In other words, plants containing transformed nucleic acid sequence are referred to as "transgenic plants". Transgenic and recombinant refer to a host organism such as a plant into which a heterologous nucleic acid molecule (e.g. the promoter, the chimeric gene or the vector as described herein) has been introduced. The nucleic acid can be stably integrated into the genome of the plant.

The transformation of wheat has been described several times in literature (for an overview see Maheshwari, Critical Reviews in Plant Science 14 (2) (1995), 149-178, Nehra et al., Plant J. 5 (1994), 285-297). Yuji Ishida et al. 2015, Methods in Molecular Biology, 1223: 189-198 describes a recent method to obtain transgenic wheat plants.

Further provided is a method of effecting anther-specific expression of a nucleic acid comprising introducing the recombinant gene described herein into the genome of a wheat plant, or providing the wheat plant according to the invention. Also provided is a method for controlling pollination of a wheat plant, for controlling the excision of a marker cassette in the production of marker-free transgenic wheat plants or for producing a commercially relevant product in a plant, comprising introducing the recombinant gene described herein into the genome of a wheat plant, or providing the wheat plant according to the invention.

The pollination of a wheat plant may be controlled by expressing or silencing an endogenous gene or a transgene to obtain or restore male sterility. Male sterility can be conferred by the expression of genes encoding RNases such as RNase T1 and Barnase, DNases such as an endonuclease or proteases such as papain, or by the expression of genes encoding enzymes which catalyze the synthesis of phytohormones such as isopentenyl transferase or auxin, or by the expression of genes encoding glucanases, lipases, lipid peroxidases, plant cell wall inhibitors (U.S. Pat. No. 5,652,354). Male fertility can be restored by expressing eg. barstar. The excision of a marker cassette in the production of marker-free transgenic wheat plants may be controlled for example by using an heterologous recombination system like Cre/loxP or FLP-FRT, transposons, meganucleases, zinc finger nucleases (see Yau et al 2013 BMC Biotechnology 13:36 for review). An anther-specific promoter is useful to obtain the excision only by cross pollination and without having the undesired effects caused by ectopic expression of recombinases in other tissues.

Yet another method is provided for the isolating cells from pollen sac tissues comprising introducing the recombinant gene herein described into the genome of a wheat plant, or providing the plant according to the invention.

Cells from pollen sac tissues may be isolated by expressing in a plant a fluorescent protein under the control of a pollen sac-specific promoter, generating protoplasts from such plant and subsequently performing fluorescence-activated cell sorting or by doing laser-capture micro-dissection. Isolating cells from pollen sac tissues is useful to study the genome, the transcriptome and/or the proteome that is specific to the pollen sac tissues.

Also provided is the use of the nucleic acid having anther-specific promoter activity described herein to regulate expression of an operably linked nucleic acid in a wheat plant, and the use of the nucleic acid having anther-specific promoter activity described herein, or the recombinant gene described herein to control pollination of a wheat plant, to control the excision of a marker cassette in the production of marker-free transgenic wheat plants or to produce a commercially relevant product in a wheat plant.

Further provided is the use of the nucleic acid having anther-specific promoter activity described herein to isolate cells from pollen sac tissues.

Also provided is the use of the isolated nucleic acid described herein to identify other nucleic acids comprising anther-specific promoter activity.

The promoter described herein can further be used to create hybrid promoters, i.e. promoters containing (parts of) one or more of the promoters(s) of the current invention and (parts of) other promoter which can be newly identified or known in the art. Such hybrid promoters may have optimized tissue specificity or expression level.

Yet another embodiment provides a method of producing food, feed, or an industrial product comprising (a) obtaining the wheat plant or a part thereof, according to the invention; and (b) preparing the food, feed or industrial product from the plant or part thereof. In another embodiment, said food or feed is meal, grain, starch, flour or protein, or said industrial product is biofuel, industrial chemicals, a pharmaceutical or a nutraceutical.

The wheat plants according to the invention may additionally contain an endogenous or a transgene, which confers herbicide resistance, such as the bar or pat gene, which confer resistance to glufosinate ammonium (Liberty®, Basta® or Ignite®) [EP 0 242 236 and EP 0 242 246 incorporated by reference]; or any modified EPSPS gene, such as the 2 mEPSPS gene from maize [EP0 508 909 and EP 0 507 698 incorporated by reference], or glyphosate acetyltransferase, or glyphosate oxidoreductase, which confer resistance to glyphosate (RoundupReady®), or bromoxynitril nitrilase to confer bromoxynitril tolerance, or any modified AHAS gene, which confers tolerance to sulfonylureas, imidazolinones, sulfonylaminocarbonyltriazolinones, triazolopyrimidines or pyrimidyl(oxy/thio)benzoates.

The plants or seeds of the plants according to the invention may be further treated with a chemical compound, such as a chemical compound selected from the following lists: Herbicides: Clethodim, Clopyralid, Diclofop, Ethametsulfuron, Fluazifop, Glufosinate, Glyphosate, Metazachlor, Quinmerac, Quizalofop, Tepraloxydim, Trifluralin. Fungicides/PGRs: Azoxystrobin, N-[9-(dichloromethylene)-1,2,3,4-tetrahydro-1,4-methanonaphthalen-5-yl]-3-(difluoromethyl)-1-methyl-1H-pyrazole-4-carboxamide (Benzovindiflupyr, Benzodiflupyr), Bixafen, Boscalid, Carbendazim, Carboxin, Chlormequat-chloride, Coniothryrium minitans, Cyproconazole, Cyprodinil, Difenoconazole, Dimethomorph, Dimoxystrobin, Epoxiconazole, Famoxadone, Fluazinam, Fludioxonil, Fluopicolide, Fluopyram, Fluoxastrobin, Fluquinconazole, Flusilazole, Fluthianil, Flutriafol, Fluxapyroxad, Iprodione, Isopyrazam, Mefenoxam, Mepiquat-chloride, Metalaxyl, Metconazole, Metominostrobin, Paclobutrazole, Penflufen, Penthiopyrad, Picoxystrobin, Prochloraz, Prothioconazole, Pyraclostrobin, Sedaxane, Tebuconazole, Tetraconazole, Thiophanate-methyl, Thiram, Triadimenol, Trifloxystrobin, *Bacillus firmus, Bacillus firmus* strain I-1582, *Bacillus subtilis, Bacillus subtilis* strain GB03, *Bacillus subtilis* strain QST 713, *Bacillus pumulis, Bacillus pumulis* strain GB34. Insecticides: Acetamiprid, Aldicarb, Azadirachtin, Carbofuran, Chlorantraniliprole (Rynaxypyr), Clothianidin, Cyantraniliprole (Cyazypyr), (beta-)Cyfluthrin, gamma-Cyhalothrin, lambda-Cyhalothrin, Cypermethrin, Deltamethrin, Dimethoate, Dinetofuran, Ethiprole, Flonicamid, Flubendiamide, Fluensulfone, Fluopyram, Flupyradifurone, tau-Fluvalinate, Imicyafos, Imidacloprid, Metaflumizone, Methiocarb, Pymetrozine, Pyrifluquinazon, Spinetoram, Spinosad, Spirotetramate, Sulfoxaflor, Thiacloprid, Thiamethoxam, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide, 1-{2-fluoro-4-methyl-5-[(2,2,2-trifluoroethyl)sulfinyl]phenyl}-3-(trifluoromethyl)-1H-1,2,4-triazol-5-amine, (1E)-N-[(6-chloropyridin-3-yl)methyl]-N'-cyano-N-(2,2-difluoroethyl)ethanimidamide, *Bacillus firmus, Bacillus firmus* strain I-1582, *Bacillus subtilis, Bacillus subtilis* strain GB03, *Bacillus subtilis* strain QST 713, Metarhizium anisopliae F52.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents, such as seed obtained by selfing or crossing, e.g. hybrid seed (obtained by crossing two inbred parental lines), hybrid plants and plant parts derived there from are encompassed herein, unless otherwise indicated.

In some embodiments, the plant cells of the invention as well as plant cells generated according to the methods of the invention, may be non-propagating cells.

The obtained plants according to the invention can be used in a conventional breeding scheme to produce more plants with the same characteristics or to introduce the same characteristic in other varieties of the same or related plant species, or in hybrid plants. The obtained plants can further be used for creating propagating material. Plants according to the invention can further be used to produce gametes, seeds, embryos, either zygotic or somatic, progeny or hybrids of plants obtained by methods of the invention. Seeds obtained from the plants according to the invention are also encompassed by the invention.

"Creating propagating material", as used herein, relates to any means know in the art to produce further plants, plant parts or seeds and includes inter alia vegetative reproduction methods (e.g. air or ground layering, division, (bud) grafting, micropropagation, stolons or runners, storage organs such as bulbs, corms, tubers and rhizomes, striking or cutting, twin-scaling), sexual reproduction (crossing with another plant) and asexual reproduction (e.g. apomixis, somatic hybridization).

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a nucleic acid which is functionally or structurally defined, may comprise additional DNA regions etc.

The sequence listing contained in the file named "BCS17-2003_ST25.txt", which is 11 kilobytes (size as measured in Microsoft Windows®), contains 2 sequences SEQ ID NO: 1 through SEQ ID NO: 2 is filed herewith by electronic submission and is incorporated by reference herein.

In the description and examples, reference is made to the following sequences:

SEQUENCES

SEQ ID NO: 1: nucleotide sequence of the promoter Pvrn1Hv.
SEQ ID NO: 2: nucleotide sequence of the T-DNA Pvrn1Hv::GUS.

EXAMPLES

Unless stated otherwise in the Examples, all recombinant DNA techniques are carried out according to standard protocols as described in Sambrook and Russell (2001) Molecular Cloning: A Laboratory Manual, Third Edition, Cold Spring Harbor Laboratory Press, NY, in Volumes 1 and 2 of Ausubel et al. (1994) Current Protocols in Molecular Biology, Current Protocols, USA and in Volumes I and II of Brown (1998) Molecular Biology LabFax, Second Edition, Academic Press (UK). Standard materials and methods for plant molecular work are described in Plant Molecular Biology Labfax (1993) by R. D. D. Croy, jointly published by BIOS Scientific Publications Ltd (UK) and Blackwell Scientific Publications, UK. Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Example 1

Generation of Expression Constructs with the Pvrn1Hv Promoter Operably Linked to the GUS Reporter Gene (Pvrn1Hv::GUS)

The promoter sequence of the vrn1 promoter (SEQ ID NO: 1 or 5' to 3' position 89 to 2086 of SEQ ID NO:2) from barley, the GUS gene (β-glucuronidase) with intron (5' to 3' position 2090 to 4115 of SEQ ID NO: 2) and a fragment of the 3' untranslated end of the nopaline synthase gene (5' to 3' position 4146 to 4406 of SEQ ID NO: 2) were assembled in a vector which contains the bar selectable marker cassette (position 4487 to 6151 of SEQ ID NO: 2) to result in the T-DNA Pvrn1Hv::GUS (SEQ ID NO: 2).

Example 2

Generation of Transgenic Wheat Plants Comprising the Pvrn1Hv::GUS

In a next step the recombinant vector comprising the expression cassette of example 1, i. e. Pvrn1Hv::GUS, were used to stably transform wheat using the method described in Yuji Ishida et al. 2015, Methods in Molecular Biology, 1223: 189-198.

Example 3

In Planta Expression Pattern of Pvrn1Hv::GUS in Wheat

The in planta expression pattern of Pvrn1Hv::GUS in the different tissues of wheat plants was monitored according to the method of Jasik et al. 2011.

No GUS activity was detected in leaves, stem, developing caryopsis, seed, germinating seed (roots, endosperm, embryo) or bract of spikelet. The GUS activity was furthermore not detected in any part of the developing caryopsis. The GUS activity was however detected in pollen sac tissue (microspore, tapetum, middle layer, endothecium, epidermis) at early spike development. These results show that the Pvrn1Hv promoter has anther-specific promoter activity in wheat.

The GUS activity in those tissues was not affected by a cold treatment, thereby indicating that the Pvrn1Hv promoter does not have cold-inducible promoter activity in wheat.

FIG. 1 shows the GUS staining in wheat plants carrying Pvrn1Hv::GUS on a developing spike and on a cross section through florets showing the anthers and the gynoecium. The Gynoecium—or ovary—is not labelled. Pollen sac tissues are labelled, including pollen mother cells. The epidermis of the pollen sac is labelled but neither the filament nor the parenchyma.

---

The invention claimed is:

1. A wheat plant cell or a wheat plant comprising a recombinant gene comprising:
   a. a nucleic acid having anther-specific promoter activity selected from the group consisting of:
      i. a nucleic acid comprising the nucleotide sequence of SEQ ID NO: 1;
      ii. a nucleic acid comprising a nucleotide sequence having at least about 95% sequence identity to SEQ ID NO: 1; or
      iii. a functional fragment of i. or ii.,
   wherein said functional fragment comprises at least 300 consecutive nucleotides of SEQ ID NO: 1,
   wherein said nucleic acid is operably linked to
   b. a heterologous nucleic acid sequence encoding an expression product of interest, wherein the heterologous nucleic acid
      i. selectively disrupts the metabolism, functioning, and/or development of stamen cells of the plant, or
      ii. controls pollination by expressing or silencing an endogenous gene or a transgene to obtain or restore male sterility,
   and optionally
   c. a transcription termination and polyadenylation sequence.

2. The plant cell or plant according to claim 1, wherein the expression product of interest is an RNA molecule capable of modulating the expression of a gene or is a protein.

3. Seeds obtainable from the plant according to claim 1, wherein the seeds comprise the recombinant gene.

4. A method of producing a transgenic wheat plant comprising the steps of:
   a. providing the wheat plant cell of claim 1; and
   b. regenerating transgenic wheat plants from said transgenic cell.

5. A method of producing food, feed, or an industrial product, the method comprising:
   a. obtaining the wheat plant or wheat plant cell of claim 1, or a part or seed of said wheat plant comprising the recombinant gene; and
   b. preparing the food, feed or industrial product from the wheat plant, or part or seed thereof, or wheat plant cell.

6. The method of claim 5 wherein
   a) the food or feed is meal, grain, starch, flour or protein; or
   b) the industrial product is biofuel, industrial chemicals, a pharmaceutical or a nutraceutical.

7. The plant cell or plant of claim 1, wherein the nucleic acid having anther-specific promoter activity is a nucleic acid comprising the nucleotide sequence of SEQ ID NO: 1.

8. The plant cell or plant of claim 1, wherein the nucleic acid having anther-specific promoter activity is a nucleic acid comprising a nucleotide sequence having at least 95% sequence identity to SEQ ID NO: 1.

9. The plant cell or plant of claim 1, wherein the nucleic acid having anther-specific promoter activity is a functional fragment of i. or ii., and
   wherein said functional fragment comprises at least 300 consecutive nucleotides of SEQ ID NO: 1.

10. The plant cell or plant of claim 9, wherein the functional fragment comprises the nucleotide sequence of SEQ ID NO: 1 from nucleotide position 1647 to nucleotide position 1947.

11. The plant cell or plant of claim 9, wherein said functional fragment comprises at least 500 consecutive nucleotides of SEQ ID NO: 1.

12. The plant cell or plant of claim 9, wherein said functional fragment comprises at least 1000 consecutive nucleotides of SEQ ID NO: 1.

13. The plant cell or plant of claim 9, wherein said functional fragment comprises at least 1200 consecutive nucleotides of SEQ ID NO: 1.

* * * * *